United States Patent
Oishi et al.

(10) Patent No.: US 8,257,567 B2
(45) Date of Patent: Sep. 4, 2012

(54) HEMOGLOBIN DETERMINATION METHOD

(75) Inventors: Kazuyuki Oishi, Osaka (JP); Izumi Omoto, Osaka (JP); Toshiki Kawabe, Osaka (JP); Eriko Kusaka, Osaka (JP)

(73) Assignee: Sekisui Chemical Co., Ltd., Osaka (JP)

( * ) Notice: Subject to any disclaimer, the term of this patent is extended or adjusted under 35 U.S.C. 154(b) by 514 days.

(21) Appl. No.: 12/311,830

(22) PCT Filed: Oct. 12, 2007

(86) PCT No.: PCT/JP2007/069936
§ 371 (c)(1),
(2), (4) Date: Jul. 15, 2009

(87) PCT Pub. No.: WO2008/047703
PCT Pub. Date: Apr. 24, 2008

(65) Prior Publication Data
US 2010/0282607 A1 Nov. 11, 2010

(30) Foreign Application Priority Data

Oct. 16, 2006 (JP) .................................. 2006-281459

(51) Int. Cl.
*B01D 57/02* (2006.01)
(52) U.S. Cl. ........................................ 204/451; 204/450
(58) Field of Classification Search .................. 204/451, 204/471, 454, 601, 450
See application file for complete search history.

(56) References Cited

U.S. PATENT DOCUMENTS

| | | | |
|---|---|---|---|
| 5,246,558 A | 9/1993 | Chevigne et al. | |
| 5,599,433 A | 2/1997 | Keo et al. | |
| 5,611,903 A | 3/1997 | Janssens et al. | |
| 6,074,541 A * | 6/2000 | Srinivasan et al. | 204/451 |
| 2006/0102478 A1 | 5/2006 | Robert et al. | |

FOREIGN PATENT DOCUMENTS

| | | |
|---|---|---|
| JP | 5-133938 | 5/1993 |
| JP | 9-105739 | 4/1997 |
| JP | 9-510792 | 10/1997 |
| JP | 2006-145537 | 6/2006 |

OTHER PUBLICATIONS

Doelman et al. Capillary electrophoresis system for hemoglobin A1c determinations evaluated, Clin Chemistry, 1997, 644-648.*
Siren et al. Direct monitoring of glycohemoglobin A1c in the blood samples of diabetic patients by capillary electrophoresis Comparison with an immunoassay method, J Chromatography, 2002,201-207.*
International Search Report issued Jan. 15, 2008 in the International (PCT) Application of which the present application is the U.S. National Stage.

* cited by examiner

*Primary Examiner* — Alex Noguerola
*Assistant Examiner* — Gurpreet Kaur
(74) *Attorney, Agent, or Firm* — Wenderoth, Lind & Ponack, L.L.P.

(57) ABSTRACT

An object of the present invention is to provide a method for measuring hemoglobin using electrophoresis, in particular a method for measuring hemoglobin that enables high accuracy measurement of stable hemoglobin A1c and a method for simultaneously measuring stable hemoglobin A1c and abnormal hemoglobins.

The present invention provides a method for measuring hemoglobin using electrophoresis, which comprises: immobilizing an ionic polymer on an inner surface of a migration path; and using a buffer solution containing a sulfated polysaccharide.

9 Claims, 4 Drawing Sheets

HEMOGLOBIN DETERMINATION METHOD

This application is a U.S. national stage of International Application No. PCT/JP2007/069936 filed Oct. 12, 2007.

TECHNICAL FIELD

The present invention relates to a method for measuring hemoglobin using electrophoresis, particularly a method for measuring hemoglobin that enables high accuracy measurement of stable hemoglobin A1c, and a method for simultaneously measuring stable hemoglobin A1c and abnormal hemoglobins.

BACKGROUND ART

Hemoglobin (hereinafter, also referred to as Hb), in particular hemoglobin A1c (hereinafter, also referred to as HbA1c) of a form of glycosylated hemoglobins reflect an average blood sugar level in past 1 to 2 months. Therefore, hemoglobin A1c is widely used in a screening test for diabetes mellitus and as a test item for checking whether a diabetic keeps the blood sugar under control.

Conventionally, HbA1c has been measured by HPLC, immunoassay, electrophoresis or the like. Especially, HPLC is widely used in clinical examinations. HPLC requires only 1 to 2 minutes to measure each sample, and has achieved a measurement accuracy of about 1.0% in terms of a CV value obtained by a within-run reproducibility test. Measurement methods for checking whether a diabetic keeps the blood sugar under control are required to perform at this level.

Meanwhile, application of an electrophoresis technique that enables high accuracy measurement of HbA1c to the clinical examinations is expected to yield a significantly advantageous effect in cost because an electrophoresis apparatus has a simple configuration, and can be formed as a low-cost small system such as a microchip-electrophoresis apparatus.

Measurement of Hb by electrophoresis has been used for a long time to separate abnormal Hbs with an unusual amino acid sequence. However, separation of HbA1c is significantly difficult, and takes 30 minutes or more by gel electrophoresis. Thus, electrophoresis has been unsatisfactory in terms of measurement time and measurement accuracy when applied to the clinical examinations. Therefore, electrophoresis has hardly been applied to clinical diagnosis of diabetes in recent years.

However, capillary electrophoresis, which was proposed in around 1990, generally enables high accuracy measurement with high separation efficiency. For example, Patent Document 1 and Patent Document 2 disclose techniques for separating HbA1c by capillary electrophoresis.

However, use of the method of Patent Document 1 does not overcome the problem of taking a long time to measure, and also may denature Hb due to use of a buffer solution with a high pH of 9 to 12. For these reasons, it has been difficult to apply this method to the clinical examinations.

In the method of Patent Document 2, two techniques that had been known prior to the publication of this Patent Document, that is, a technique using the affinity of sulfated polysaccharides to Hb, and a dynamic coating technique of an inside of a capillary are used in combination. This method enables measurement in a shorter time compared to gel electrophoresis, and takes only about 10 minutes to measure.

However, such a dynamic coating technique requires coating the inside of the capillary after each measurement for the following measurement. Therefore, in order to coat the inside of the capillary in the same way at the time of the beginning of each measurement, it is necessary to remove the coating layer by washing after each measurement to return the inside of the capillary to the initial condition that is the condition before the measurement. Namely, for repetitive measurement, washing and coating procedure needs to be performed between each measurement, resulting in an increase in the measurement time. The washing and coating procedure may also cause a measurement error. In addition, a reagent for coating needs to be prepared for the measurement, leading to a disadvantage in cost. Even when not used for the repetitive measurement, the technique takes about 10 minutes to measure, which is much longer than needed in HPLC, and is unsatisfactory for application to the clinical examinations.

For clinical diagnosis of diabetes, stable HbA1c, which is a type of HbA1c and used as a diabetic indicator, should be separated from substances that disturb measurement such as unstable HbA1c and carbamylated Hbs (hereafter, also referred to as modified Hbs). However, electropherograms obtained by the methods disclosed in Patent Document 1 and Patent Document 2 were unsatisfactory in terms of separation performance and measurement accuracy, and it has been difficult to separate stable HbA1c from the modified Hbs by the techniques within the scope of these methods.

Abnormal Hbs are present in some samples, and known as a diagnostic indicator of a disease due to hemoglobin defect such as hemolytic anemia and thalassemia. Techniques using HPLC for measuring HbA1c have been developed to provide simultaneous measurement of stable HbA1c and the abnormal Hbs. However, such technique using electrophoresis has not been proposed so far.

Patent Document 1: Japanese Kohyo Publication No. Hei-09-510792
Patent Document 2: Japanese Kokai Publication No. Hei-09-105739

DISCLOSURE OF THE INVENTION

Problems to be Solved by the Invention

In view of the above-mentioned problems, the present invention aims to provide a method for measuring hemoglobin using electrophoresis, particularly a method for measuring hemoglobin that enables high accuracy measurement of hemoglobin A1c, and a method for simultaneously measuring stable hemoglobin A1c and abnormal hemoglobins.

Means for Solving the Problems

The present inventors conducted intensive studies to find out that immobilization of an ionic polymer on a migration path and use of a buffer solution containing a sulfated polysaccharide enable high accuracy measurement of hemoglobin, in particular stable HbA1c in a short time, and thus completed the present invention.

The present invention relates to a method for measuring hemoglobin using electrophoresis that comprises immobilizing an ionic polymer on a migration path; and using a buffer solution containing a sulfated polysaccharide.

Hereinafter, the present invention is described in detail.

An electrophoresis apparatus that can implement the method for measuring hemoglobin of the present invention is not particularly limited, and examples thereof include electrophoresis apparatuses generally called capillary electrophoresis apparatuses, electrophoresis apparatuses generally called microchip-electrophoresis apparatuses, and the like.

FIG. 7 shows an example of a capillary electrophoresis apparatus used in the method for measuring hemoglobin of the present invention. As shown in FIG. 7, the capillary electrophoresis apparatus 11 is provided with an anode reservoir 12, a cathode reservoir 13, a capillary 14, a high-voltage power supply 15, a detector 16, and a pair of electrodes 17 and 18. Each end of the capillary 14 is immersed in a buffer solution in the anode reservoir 12 or the cathode reservoir 13, and the inside of the tubular capillary 14 is filled with the buffer solution. The electrodes 17 and 18 are electrically connected with the high-voltage power supply 15.

In the method for measuring hemoglobin of the present invention, an ionic polymer is immobilized on the inner surface of the capillary 14 that serves as a migration path. For measurement of hemoglobin, a sample is injected into the capillary 14 from one end, and a predetermined voltage is applied by the high-voltage power supply 15 to measure a target substance traveling in the capillary 14 with the detector 16.

In the method for measuring hemoglobin of the present invention, the ionic polymer to be immobilized on the migration path has an ionic group in the polymer that is a base material, and examples thereof include anionic polymers and cationic polymers.

The anionic polymer has an anionic group in the polymer. The anionic polymer is desirably hydrophilic, and specific examples thereof include polysaccharides containing an anionic group, organic synthetic polymers containing an anionic group, and the like.

The anionic group is not particularly limited, and examples thereof include carboxyl group, phosphate group, sulfonic group and the like.

Examples of the polysaccharides containing an anionic group include known polysaccharides containing an anionic group, and the like. Examples of the known polysaccharides containing an anionic group include polysaccharides containing a sulfate group such as chondroitin sulfate, dextran sulfate, heparin, heparan and fucoidan, and salts thereof; polysaccharides containing a carboxyl group such as alginic acid and pectic acid, and salts thereof; compounds for introducing an anionic group to a neutral polysaccharide such as cellulose, dextran, agarose, mannan or starch, or a derivative thereof, and salts thereof; and the like.

Examples of the organic synthetic polymers containing an anionic group include known organic synthetic polymers containing an amino group, and the like. Examples of the known organic synthetic polymer containing an amino group include poly(meth)acrylic acids, poly(meth)acrylates containing a phosphate group, poly(meth)acrylates containing a sulfonic group, poly(2-acrylamide-butyl sulfonic acid), copolymers thereof, and the like.

The desirable lower limit of the molecular weight of the anionic polymer is 500 Da. In the case where the molecular weight of the anionic polymer is less than 500 Da, it is difficult to sufficiently coat the inner surface of the migration path, possibly leading to poor separation performance.

The cationic polymer has a cationic group in the polymer. The cationic polymer is desirably hydrophilic, and specific examples thereof include aminated polysaccharides, organic synthetic polymers containing an amino group, and the like.

The cationic group is not particularly limited, and examples thereof include primary, secondary, tertiary and quaternary amino groups, and the like.

Examples of the aminated polysaccharides include known aminated polysaccharides, and the like. Examples of the known aminated polysaccharides include chitosan derivatives such as chitin and chitosan, and salts thereof; N-substituted cellulose derivatives such as amino cellulose and N-methylamino cellulose, and salts thereof; compounds for introducing an amino group to a neutral polysaccharide such as dextran, agarose, mannan or starch, or a derivative thereof, and salts thereof; and the like.

Examples of the organic synthetic polymer containing an amino group include known organic synthetic polymers containing an amino group and the like. Examples of the known organic synthetic polymer containing an amino group include polyethyleneimine, polybrene, and poly(meth)acrylates containing an amino group such as poly 2-diethylaminoethyl (meth)acrylate, copolymers thereof, and the like.

The desirable lower limit of the molecular weight of the cationic polymer is 500 Da. In the case where the molecular weight of the cationic polymer is less than 500 Da, it is difficult to sufficiently coat the inner surface of the migration path, possibly leading to poor separation performance.

In the method for measuring hemoglobin of the present invention, the "migration path" is defined as a part of a flow channel for electrophoresis in which a measurement sample is moved and/or separated by electrophoresis (a part from a position at which a measurement sample is injected to a position at which components of the sample are detected). Specific examples are as follows: In capillary electrophoresis, the migration path is defined as a part of a capillary from a position at which a sample is injected to a position at which components of the sample are detected by a detector. In microchip electrophoresis, the migration path is defined as a part of a flow channel on a microchip from a position at which a sample is injected to a position at which components of the sample are detected by a detector in a microchip-electrophoresis apparatus.

Specifically, the inner surface of the migration path is defined, for example, in capillary electrophoresis, as the inner surface of the migration path of the capillary, and in microchip electrophoresis, as the inner surface of the migration path of the flow channel on the microchip in the microchip-electrophoresis apparatus.

A material forming the migration path is not particularly limited, and examples thereof include glasses, metals, resins and the like. Especially, glasses or resins are desirable.

Solid matters such as particles of packing materials may be present in the migration path, but are desirably not present in the migration path.

The desirable lower limit of the length of the migration path is 10 mm, and the desirable upper limit thereof is 300 mm. In the case where the length of the migration path is less than 10 mm, a sample may be insufficiently separated, which in turn may prevent accurate measurement. In the case where the length of the migration path is more than 300 mm, it may take longer to measure, or an obtained electropherogram may have a deformed peak, which in turn may prevent accurate measurement. The more desirable lower limit is 20 mm, and the more desirable upper limit is 200 mm.

The desirable lower limit of the width or the diameter of the migration path is 1 μm, and the desirable upper limit thereof is 200 μm. In the case where the width or the diameter of the migration path is less than 1 μm, the optical path length for detecting sample components is short, possibly leading to low measurement accuracy. In the case where the width or the diameter of the migration path is more than 200 μm, an obtained electropherogram may have a broad peak due to diffusion of the sample inside the migration path, possibly leading to low measurement accuracy.

A known method can be used to immobilize the ionic polymer on the migration path. Specific examples include: a method in which the ionic polymer is allowed to contact the inner surface of the migration path and to physically adsorb thereon by a hydrophobic or electrostatic interaction or the like; a method in which the ionic polymer is immobilized on the inner surface of the migration path by a covalent bond between respective functional groups of the inner surface and the ionic polymer, or a covalent bond via another substance and the like; and the like. When the ionic polymer is treated using such a method and subjected to, for example, a heating process, a drying process and the like to be immobilized, the immobilized ionic polymer is less likely to peel off and allows repetition of the measurement.

Another layer may be provided between the ionic polymer layer and the inner surface of the migration path as long as the ionic polymer layer forms the innermost surface of the migration path in the end.

The ionic polymer to be immobilized is desirably provided, although depending on the type of the ionic polymer or the immobilizing method, in the form of an about 0.01 to 20% solution in the above-mentioned procedure. In the case where the ionic polymer concentration is less than 0.01%, the ionic polymer may be insufficiently immobilized. However, in the case where the ionic polymer concentration is more than 20%, the formed immobilized layer may be uneven and peel off during the measurement, which in turn may cause a reduction in reproducibility.

In the method for measuring hemoglobin of the present invention, a buffer solution containing a sulfated polysaccharide is used.

In the method for measuring hemoglobin of the present invention, in addition to a buffer solution filling the migration path for electrophoresis and buffer solutions filling the anode reservoir and the cathode reservoir set for the ends of the migration path for electrophoresis, the buffer solution includes a hemolysing agent for dissolving and diluting a measurement sample, and other buffer solutions such as a buffer solution for washing the inside of the flow channel, and the like.

In the method for measuring hemoglobin of the present invention, all these buffer solutions may contain a sulfated polysaccharide, or only some of the buffer solutions may contain a sulfated polysaccharide.

A solution containing a known buffer composition having buffer capacity can be used as the buffer solution, and specific examples thereof include organic acids such as citric acid, succinic acid, tartaric acid, and malic acid and salts thereof; amino acids such as glycine, taurine and arginine; inorganic acids such as hydrochloric acid, nitric acid, sulfuric acid, phosphoric acid, boric acid and acetic acid, and salts thereof; and the like.

Optionally, a generally used additive may be added to the above-mentioned buffer solution. Examples thereof include surfactants, various polymers, hydrophilic low-molecular-weight compounds, and the like.

The sulfated polysaccharide is not particularly limited, and a known sulfated polysaccharide can be used. Specific examples include compounds for introducing a sulfate group to a neutral polysaccharide such as cellulose, dextran, agarose, mannan or starch, or a derivative thereof, and salts of thereof; chondroitin sulfate; dextran sulfate; heparin; heparan; fucoidan; and the like.

The desirable lower limit of the sulfated polysaccharide content of the buffer solution is 0.01% by weight, and the desirable upper limit thereof is 10.0% by weight. In the case where the sulfated polysaccharide content is less than 0.01% by weight, the addition effect of the sulfated polysaccharide is less likely to be produced, leading to insufficient separation. On the other hand, in the case where the sulfated polysaccharide content is more than 10.0% by weight, problems such as an increase in the measurement time and insufficient separation may occur.

In the method for measuring hemoglobin of the present invention, a target hemoglobin is not particularly limited, and examples thereof include conventionally known hemoglobins. Specific examples include $HbA_0$, HbA1a, HbA1b, stable HbA1c, unstable HbA1c, and HbF (fetal Hb); modified Hbs such as acetylated Hbs and carbamylated Hbs; and abnormal Hbs such as HbS and HbC; and the like. The method for measuring hemoglobin of the present invention enables separation of, in particular, stable HbA1c that can be used as an indicator for diagnosis of diabetes from unstable HbA1c, the modified Hbs such as carbamylated Hbs, and the like, and measurement of stable HbA1c. Such a method for measuring stable hemoglobin A1c using the method for measuring hemoglobin of the present invention is also one aspect of the present invention.

The use of the method for measuring hemoglobin of the present invention enables simultaneous measurement of $HbA_0$, HbA1a, HbA1b, unstable HbA1c, and HbF (fetal Hb) with stable HbA1c.

The use of the method for measuring hemoglobin of the present invention also enables simultaneous measurement of HbA2 that can be used as an indicator of diagnosis of a disease other than diabetes with stable HbA1c.

Moreover, the use of the method for measuring hemoglobin of the present invention also enables simultaneous measurement of the abnormal Hbs such as HbS and HbC that can be used as an indicator of diagnosis of a disease other than diabetes with stable HbA1c. The simultaneous measurement of stable HbA1c and HbA2 or the abnormal Hbs can provide an indicator of diagnosis of diabetes and a disease other than diabetes.

Such a method for simultaneously measuring stable hemoglobin A1c and abnormal hemoglobins using the method for measuring hemoglobin of the present invention is also one aspect of the present invention.

Effects of the Invention

According to the present invention, immobilization of an ionic polymer on an inner surface of a migration path enables measurement of hemoglobin, in particular stable HbA1c in a short time of a few minutes per sample with a high accuracy of about 1.0% in terms of a CV value indicating within-run reproducibility. Therefore, it is possible to suitably used in controlling an HbA1c value of a diabetic using electrophoresis, which has been difficult in the conventional art. This is owing to an unexpected effect that a component that could not have been separated in the conventional art can be separated, not a generally expected effect that the measurement time is reduced by using the coating method by immobilization instead of the dynamic coating technique.

The immobilization of the ionic polymer on the inner surface of the migration path can avoid procedure such as a coating process after each measurement, and thereby enables measurement in a shorter time. The immobilization of the ionic polymer on the inner surface of the migration path also avoids use of a coating agent, and thereby provides a significant advantage in cost.

Moreover, since an apparatus used in electrophoresis has a simpler configuration than that used in HPLC, the use of the method for measuring hemoglobin of the present invention can provide a method for measuring hemoglobin that allows low cost measurement.

Additionally, the abnormal Hbs and the like that can be used as an indicator of a disease other than diabetes can be measured simultaneously with stable HbA1c.

BEST MODE FOR CARRYING OUT THE INVENTION

Hereinafter, the present invention will be described in detail by way of examples. However, the present invention is not limited only to these examples.

Example 1

An aqueous solution containing 0.2% by weight of dextran sulfate (produced by Wako Pure Chemical Industries, Ltd.) as an anionic polymer was prepared. Next, 0.2N-NaOH, an ion exchange water, and 0.5N-HCl were allowed to flow through a capillary made of fused silica (produced by GL Sciences, Inc.: 25 μm in inside diameter×30 cm in full length) in this order to wash the inside of the capillary, and then the obtained dextran sulfate aqueous solution was allowed to flow through the capillary for 20 minutes. Subsequently, air was injected into the capillary to send out the dextran sulfate aqueous solution, and then the capillary was dried in a drier at a temperature of 40° C. for 12 hours. Thereafter, the dextran sulfate aqueous solution was injected again, and the procedure of injection of air and drying was repeated 5 times.

The obtained dextran-sulfate-immobilized capillary was set in a capillary electrophoresis apparatus (PA/CE MDQ, produced by Beckman Coulter, Inc.). Subsequently, a citrate buffer solution (pH 4.7) containing 2% by weight of chondroitin sulfate (produced by Wako Pure Chemical Industries, Ltd.: sulfated polysaccharide) as a sulfated polysaccharide was set for each end of the capillary to fill the inside of the capillary with the buffer solution.

(Measurement of Healthy Human Blood)

A blood sample was collected from a healthy human with heparin. To 70 μL of this healthy human whole blood sample was added 200 μL of a citrate buffer solution (pH 6.0) containing 2.0% by weight of chondroitin sulfate as a sulfated polysaccharide to hemolyze and dilute the blood sample. The sample thus obtained was used as a measurement sample.

The sample was injected into the capillary from one end, and subjected to electrophoresis by applying a voltage of 20 kV to the buffer solutions set for the ends of the capillary to measure transition of visible light absorbance at 415 nm. Thus, stable HbA1c in human blood was measured by capillary electrophoresis. FIG. 1 shows the obtained electropherogram. In FIG. 1, the peak 1 represents stable HbA1c, and the peak 2 represents HbA$_0$. Here, stable HbA1c could be separated in about 1.5 minute electrophoresis run.

(Measurement of Sample Containing Modified Hb)

Glucose was added to the healthy human whole blood sample used in the measurement of healthy human blood to give a concentration of 2000 mg/dL. Thus, a sample containing a large amount of unstable HbA1c that is a form of modified Hbs was artificially prepared. FIG. 2 shows the obtained electropherogram. In FIG. 2, the peak 1 represents stable HbA1c, the peak 2 represents HbA$_0$, and the peak 3 represents the modified Hb (unstable HbA1c). As shown in FIG. 2, stable HbA1c and unstable HbA1c that is a form of modified Hbs were favorably separated.

Example 2

The inner surface of the capillary was coated using a 0.5% by weight aqueous solution of polymethacrylic acid that is an anionic polymer by following the same method as in Example 1. Thereafter, a healthy human blood sample and a sample containing the modified Hb were measured by capillary electrophoresis by following the same method as in Example 1, except that a malate buffer solution containing 2.0% by weight of dextran sulfate as a sulfated polysaccharide was used as a buffer solution. The obtained electropherograms were similar to those shown in FIG. 1 and FIG. 2.

Example 3

A cross-shaped migration path was formed on a glass microchip (30 mm×20 mm×2 mm), and a buffer solution reservoir was set for each end of the migration path.

The inner surface of the migration path was coated using chondroitin sulfate as an anionic polymer (1.0% by weight aqueous solution) by following the same method as in Example 1. Thereafter, a healthy human blood sample and a sample containing the modified Hb were measured by microchip electrophoresis at 1000 V using the same buffer solutions as those used in Example 1. The obtained electropherograms were similar to those shown in FIG. 1 and FIG. 2.

Example 4

The inner surface of the capillary was coated using a 0.2N hydrochloric acid solution containing 0.2% by weight of chitosan (chitosan 100, produced by Wako Pure Chemical Industries, Ltd.) as a cationic polymer by following the same method as in Example 1. Thereafter, a healthy human blood sample and a sample containing the modified Hb were measured by capillary electrophoresis by following the same method as in Example 1, except that a citrate buffer solution containing 2.0% by weight of chondroitin sulfate as a sulfated polysaccharide was used as a buffer solution. The obtained electropherograms were similar to those shown in FIG. 1 and FIG. 2.

Example 5

The inner surface of the capillary was coated using a 0.5% by weight aqueous solution of polybrene (produced by Nacalai Tesque, Inc.) as a cationic polymer by following the same method as in Example 1. Thereafter, a healthy human blood sample and a sample containing the modified Hb were measured by capillary electrophoresis by following the same method as in Example 1, except that a malate buffer solution containing 2.0% by weight of dextran sulfate as a sulfated polysaccharide was used as a buffer solution. The obtained electropherograms were similar to those shown in FIG. 1 and FIG. 2.

Example 6

A cross-shaped migration path was formed on a polydimethylsiloxane microchip (30 mm×20 mm×2 mm), and a buffer solution reservoir was set for each end of the migration path.

The inner surface of the migration path was coated using chitosan (1.0% by weight aqueous solution) as a cationic polymer by following the same method as in Example 3. Thereafter, a healthy human blood sample and a sample containing the modified Hb were measured by microchip electrophoresis by following the same procedure as in Example 3, except that a malate buffer solution containing 2.0% by weight of dextran sulfate as a sulfated polysaccharide was used as a buffer solution. The obtained electropherograms were similar to those shown in FIG. 1 and FIG. 2.

Comparative Example 1

Measurement was carried out using a dynamic coating technique in which an anionic polymer was not immobilized on an inner surface of a capillary but was allowed to flow through the capillary immediately before the measurement.

Namely, 0.2N-NaOH, an ion exchange water, and 0.5N-HCl were allowed to flow through a capillary made of fused silica (produced by GL Sciences, Inc.: 25 μm in inside diameter×30 cm in full length) in this order to wash the inside of the capillary, and then the dextran sulfate aqueous solution used in Example 1 was allowed to flow through the capillary for 1 minute.

Subsequently, a malate buffer solution (pH 4.7) containing 2.0% by weight of chondroitin sulfate (produced by Wako Pure Chemical Industries, Ltd.: sulfated polysaccharide) was set for each end of the capillary to fill the capillary with the buffer solution. Thereafter, a sample containing the modified Hb was measured by following the same method as in Example 1. No peak was detected in the obtained electropherogram.

Comparative Example 2

Measurement was carried out using a dynamic coating technique in which a cationic polymer was not immobilized on an inner surface of a capillary but was allowed to flow through the capillary immediately before the measurement.

Namely, 0.2N NaOH, an ion exchange water, and 0.5N HCl were allowed to flow through a capillary made of fused silica (produced by GL Sciences, Inc.: 25 μm in inside diameter×30 cm in full length) in this order to wash the inside of the capillary, and then the chitosan solution obtained in Example 1 was allowed to flow through the capillary for 1 minute to dynamically coat the inner surface of the capillary.

Next, a malate buffer solution (pH 4.7) containing 2.0% by weight of chondroitin sulfate (produced by Wako Pure Chemical Industries, Ltd.: sulfated polysaccharide) was set for each end of the capillary to allow the buffer solution to flow through the capillary.

Thereafter, a sample containing the modified Hb was measured by following the same method as in Example 1, and an electropherogram shown in FIG. 3 was obtained. In FIG. 3, the peak 1 represents stable HbA1c, the peak 2 represents HbA$_0$, and the peak 3 represents the modified Hb (unstable HbA1c). As shown in FIG. 3, the peak 1 representing stable HbA1c overlaps the peak 3 representing the modified Hb. Namely, stable HbA1c could not be separated.

Comparative Example 3

Measurement was carried out using a dynamic coating technique in which a cationic polymer was not immobilized on an inner surface of a capillary but was allowed to flow through the capillary immediately before the measurement. Namely, 0.2N NaOH, an ion exchange water, and 0.5N HCl were allowed to flow through a capillary made of fused silica (produced by GL Sciences, Inc.: 25 μm in inside diameter×23 cm in full length) in this order to wash the inside of the capillary, and then a malate buffer solution containing 0.5% by weight of albumin (horse origin: produced by Wako Pure Chemical Industries, Ltd.) was allowed to flow through the capillary for 1 minute. Next, a malate buffer solution (pH 4.7) containing 0.2% by weight of chondroitin sulfate (produced by Wako Pure Chemical Industries, Ltd.: sulfated polysaccharide) was set for each end of the capillary to allow the buffer to flow through the capillary. A sample was injected into the capillary from one end, and subjected to electrophoresis by applying a voltage of 8.5 kV to the buffer solutions set for the ends of the capillary to measure transition of visible light absorbance at 415 nm. Thus, the sample containing the modified Hb was measured. The obtained electropherogram was similar to that shown in FIG. 3. Namely, stable HbA1c could not be separated from the modified Hb.

Comparative Example 4

A healthy human blood was subjected to electrophoresis by following the same procedure as in Example 4, except that a citrate buffer solution (pH 4.7) without chondroitin sulfate was used as a buffer solution. No peak was detected in the obtained electropherogram.

Comparative Example 5

A healthy human blood sample was subjected to electrophoresis by following the same procedure as in Example 6, except that a malate buffer solution (pH 4.7) without dextran sulfate was used as a buffer solution. No peak was detected in the obtained electropherogram.

(Evaluation)
(1) Evaluation of Modified Hb Separation Performance

Samples containing a modified Hb were prepared from a healthy human blood sample. Namely, a sample containing unstable HbA1c was prepared by adding glucose to the healthy human blood to give a concentration of 2000 mg/dL by following the same procedure as in Example 1, and a sample containing a carbamylated Hb was prepared by adding sodium cyanate to give a concentration of 50 mg/dL. The healthy human blood sample and the respective samples containing one of the modified Hbs were measured under the respective measurement conditions of Examples 1 to 6 and Comparative Examples 2 and 3 to determine a stable HbA1c value of each sample.

The stable HbA1c value of each sample was calculated as a ratio (%) of an area of the stable HbA1c peak to a total area of all the hemoglobin peaks.

A value (ΔHbA1c value) was calculated by subtracting the obtained stable HbA1c value of the healthy human blood sample from the obtained stable HbA1c value of each of the samples containing the modified Hb.

Table 1 shows the results.

The samples of Comparative Examples 1 and 4 were not measured because the peak of stable HbA1c was not detected.

TABLE 1

| | Stable HbA1c value (%) | | | ΔHbA1c value (%) (difference between stable HbA1c value of sample containing modified Hb and stable HbA1c value of healthy human blood sample) | |
|---|---|---|---|---|---|
| | healthy human blood sample | Sample containing modified Hb | | | |
| | (without modified Hb) | Sample containing unstable HbA1c | Sample containing carbamylated Hb | Sample containing unstable HbA1c | Sample containing carbamylated Hb |
| Example 1 | 4.4 | 4.4 | 4.5 | 0.0 | 0.1 |
| Example 2 | 4.3 | 4.3 | 4.4 | 0.0 | 0.1 |
| Example 3 | 4.3 | 4.4 | 4.5 | 0.1 | 0.2 |
| Example 4 | 4.6 | 4.6 | 4.7 | 0.0 | 0.1 |
| Example 5 | 4.7 | 4.6 | 4.9 | −0.1 | 0.2 |
| Example 6 | 4.7 | 4.8 | 4.5 | 0.1 | −0.2 |
| Comparative Example 2 | 5.1 | 5.9 | 6.2 | 0.8 | 1.1 |
| Comparative Example 3 | 4.9 | 5.3 | 3.6 | 0.7 | −1.3 |

As shown in Table 1, the differences in each pair of the stable HbA1c values of each sample containing one of the modified Hbs and the healthy human blood sample without the modified Hbs measured under the respective measurement conditions of Examples 1 to 6 were slight and 0.2% or less. Accordingly, the results reveal that stable HbA1c could be accurately measured even under the presence of the modified Hbs.

On the contrary, in Comparative Examples 2 and 3, the differences in each pair of the measured values were within a range of 0.7 to 1.3% due to insufficient separation of the modified Hbs and stable HbA1c. Accordingly, the results reveal that the stable HbA1c value could not be accurately measured in the case where the modified Hbs were contained.

(2) Within-Run Reproducibility Test

One healthy human blood sample was continuously measured 10 times under the respective measurement conditions of Examples 1 to 6 and Comparative Examples 2 and 3, and a CV value of the obtained stable HbA1c values was calculated.

The CV value was determined by dividing the standard deviation by the average value.

Here, in each of Comparative Examples 2 and 3, a 0.2N NaOH solution was allowed to flow through the capillary for 1 minute after each measurement, and then the buffer solution for electrophoresis was allowed to flow through the capillary for 2 minutes to wash the inside of the capillary. Thereafter, the coating solution was allowed to flow through the capillary for 1 minute again to dynamically coat the inner surface of the capillary, and then the sample was injected for the following measurement. Thus, the measurement was repeated for the within-run reproducibility test.

Table 2 shows the results.

(3) Durability Test

One healthy human blood sample was continuously measured 100 times under the respective measurement conditions of Examples 1 to 6 and Comparative Examples 2 and 3 to obtain stable HbA1c values, and the difference (R value) between the maximum value and the minimum value of the obtained stable HbA1c values was calculated. Table 2 shows the results.

TABLE 2

| | Repeatability Test CV (%) | Durability test R value |
|---|---|---|
| Example 1 | 1.1 | 0.3 |
| Example 2 | 0.9 | 0.2 |
| Example 3 | 1.1 | 0.3 |
| Example 4 | 1.0 | 0.3 |
| Example 5 | 1.0 | 0.3 |
| Example 6 | 0.9 | 0.2 |
| Comparative Example 2 | 5.2 | 1.4* |
| Comparative Example 3 | 4.1 | 1.6** |

*Determined from values obtained by 50 times measurement
**Determined from values obtained by 60 times measurement As shown in Table 2, the CV value indicating the data variation was as good as about 1% in the within-run reproducibility test of Examples 1 to 6. The results reveal that Examples 1 to 6 achieved a level that can be used in controlling of the stable HbA1c value of diabetics. The variation range of the results of the 100 times repeated measurement of one sample in the durability test was also significantly small and within a range of about 0.2 to 0.3%. Accordingly, the results reveal that the use of the measurement conditions of Examples 1 to 6 makes it possible to separate stable HbA1c with high accuracy, and to stably measure the stable HbA1c value even when the measurement is repeatedly carried out.

On the contrary, in the within-run reproducibility test under the measurement conditions of Comparative Examples 2 and 3, the CV values were significantly large and completely unsatisfactory when used in controlling of the HbA1c value of diabetics. In the durability test, the measured values gradually varied as the measurement was repeated, and finally had a great variation range (R value). Under the conditions of Comparative Example 2, the measurement could not be continued after repetition of about 50 times. Under the conditions of Comparative Example 3, the measurement could not be continued after repetition of about 60 times.

(4) Measurement of Abnormal Hb

A sample containing abnormal Hbs was measured by following the same measurement conditions as the respective measurement conditions of Example 1 and Comparative Example 2, except that the used sample was an AFSC hemocontrol (produced by Helena Laboratories), which contains abnormal Hbs.

FIG. 4 shows an electropherogram obtained by the measurement under the measurement conditions of Example 1. FIG. 5 shows an electropherogram obtained by the measurement under the measurement conditions of Comparative Example 2. In each of FIG. 4 and FIG. 5, the peak 1 represents stable HbA1c, the peak 2 represents HbA$_0$, the peak 4 represents HbF (fetal Hb), the peak 5 represents HbS, and the peak 6 represents HbC. Electropherograms obtained under the respective measurement conditions of Examples 2 to 6 had the substantially same shape as that shown in FIG. 4.

As shown in FIG. 4, HbS and HbC (abnormal Hbs) as well as stable HbA1c were separated with excellent accuracy in a short time in the measurement under the measurement conditions of Example 1.

However, as shown in FIG. 5, HbS and HbC (abnormal Hbs) could not be separated in the measurement under the measurement conditions of Comparative Example 2.

Accordingly, the results reveal that the use of the measurement conditions of Examples 1 to 6 enables a screening test of a disease due to Hb defect other than diabetes simultaneously with diagnosis of diabetes by measuring stable HbA1c.

(5) Measurement of Sample Containing HbA2

A sample containing HbA2 was measured by following the same measurement conditions as those of Example 1, except that the used sample was an A2 control (level 2) (produced by Bio-Rad Laboratories, Inc.), which contains HbA2.

FIG. 6 shows the obtained electropherogram. In FIG. 6, the peak 1 represents stable HbA1c, the peak 2 represents HhA$_0$, the peak 4 represents HbF (fetal Hb), and the peak 7 represents HbA2. Electropherograms obtained by the measurement under the respective measurement conditions of Examples 2 to 6 had the substantially same shape as that shown in FIG. 6.

As shown in FIG. 6, HbA2 could be separated and stable HbA1c and HbA2 could be simultaneously measured in the measurement under the measurement conditions of Example 1.

However, HbA2 could not be separated in the measurement under the measurement conditions of Comparative Example 2.

Accordingly, the results reveal that the use of the measurement conditions of Examples 1 to 6 enables a screening test of a disease due to Hb defect other than diabetes simultaneously with diagnosis of diabetes by measuring stable HbA1c.

INDUSTRIAL APPLICABILITY

The present invention can provide a method for measuring hemoglobin using electrophoresis, particularly, a method for measuring hemoglobin that enables high accuracy measurement of stable hemoglobin A1c, and a method for simultaneously measuring stable hemoglobin A1c and abnormal hemoglobins.

Figure 1:
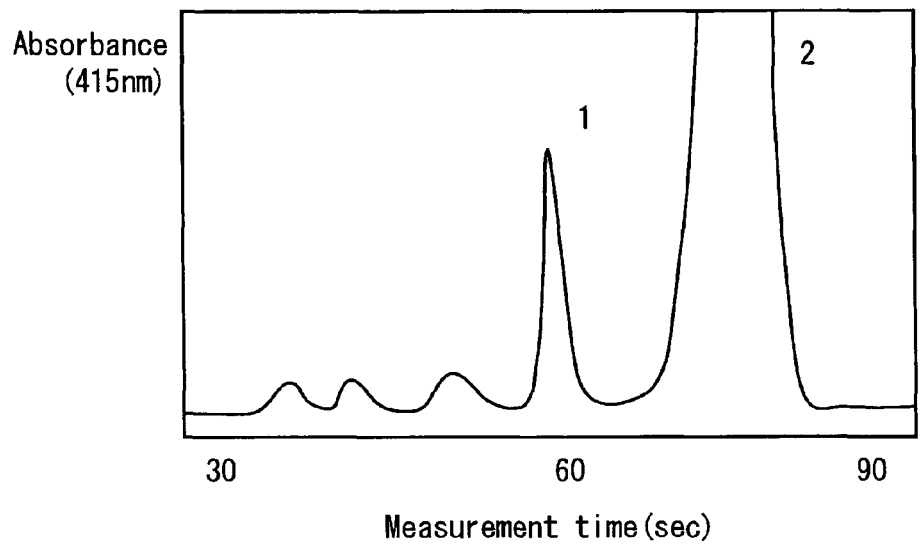
FIG. 1 is an electropherogram obtained by measurement of a healthy human blood sample under measurement conditions of Example 1.
Figure 2:
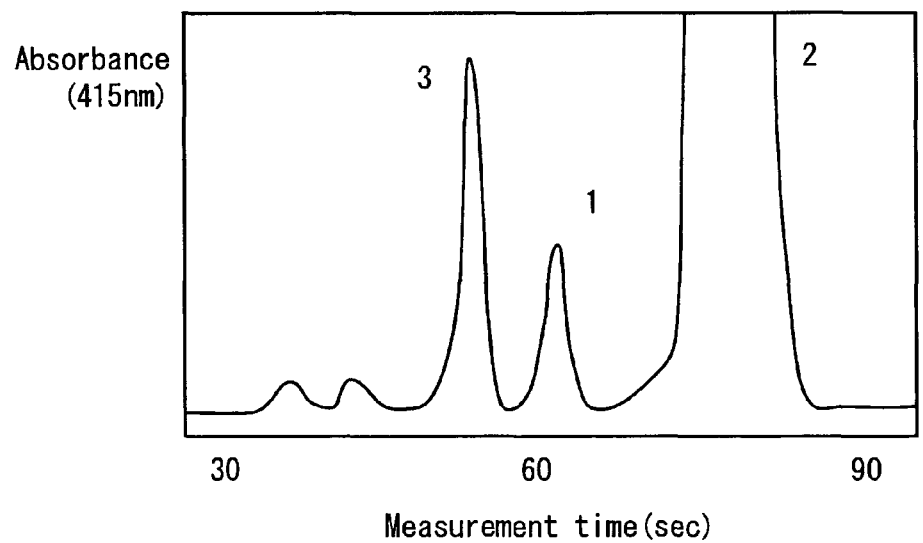
FIG. 2 is an electropherogram obtained by measurement of a sample containing a modified Hb (unstable HbA1c) under the measurement conditions of Example 1.
Figure 3:
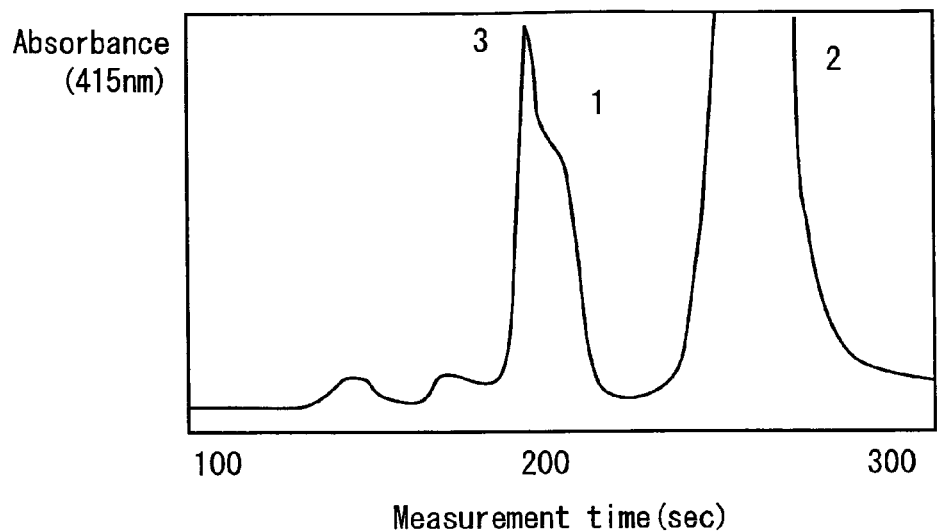
FIG. 3 is an electropherogram obtained by measurement of a sample containing the modified Hb (unstable HbA1c) under measurement conditions of Comparative Example 2.
Figure 4:
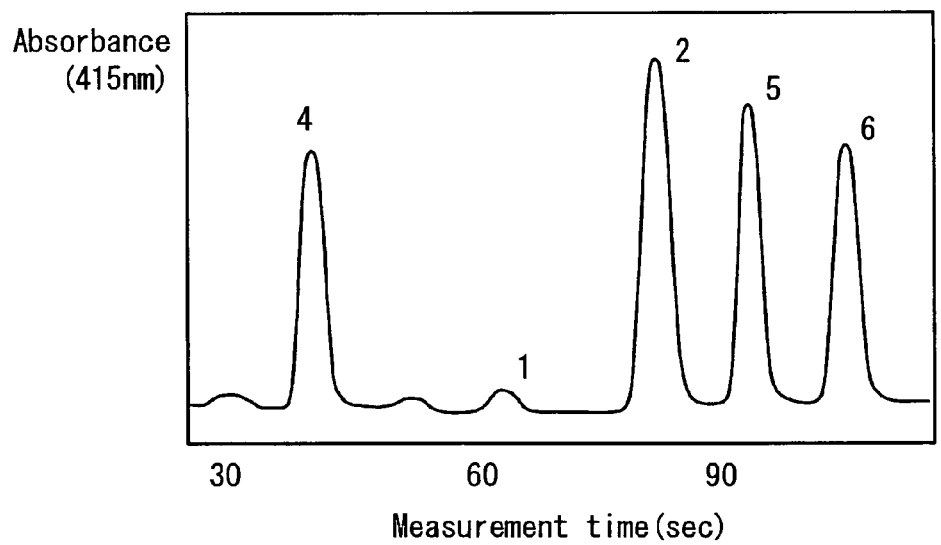
FIG. 4 is an electropherogram obtained by measurement of a sample containing abnormal Hbs (HbS and HbC) under the measurement conditions of Example 1.
Figure 5:
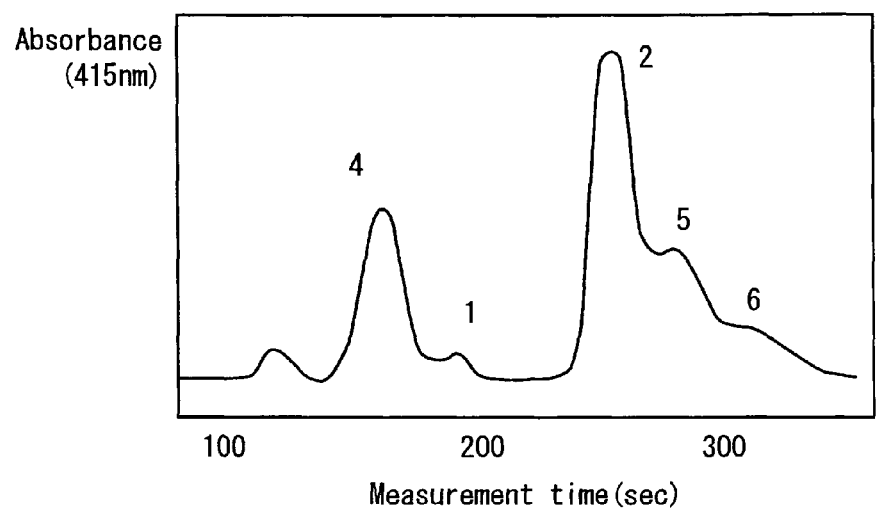
FIG. 5 is an electropherogram obtained by measurement of a sample containing the abnormal Hbs (HbS and HbC) under the measurement conditions of Comparative Example 2.
Figure 6:
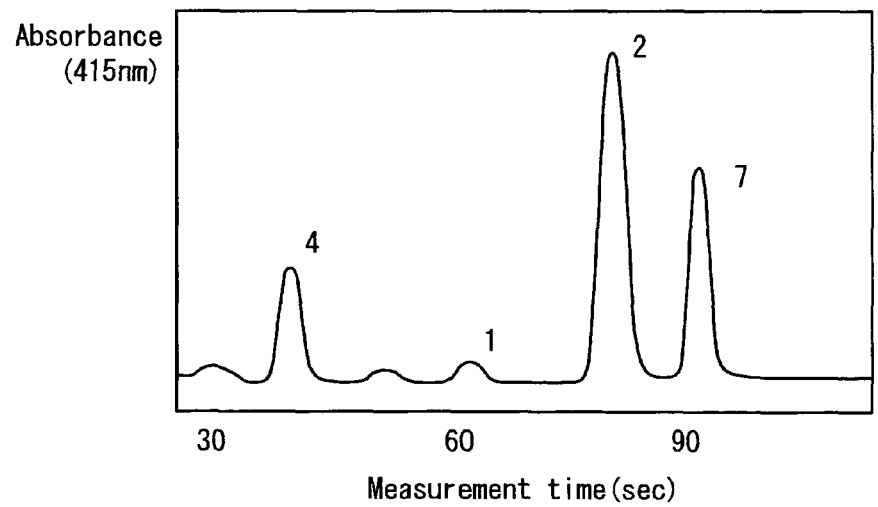
FIG. 6 is an electropherogram obtained by measurement of a sample containing HbA2 under the measurement conditions of Example 1.
Figure 7:
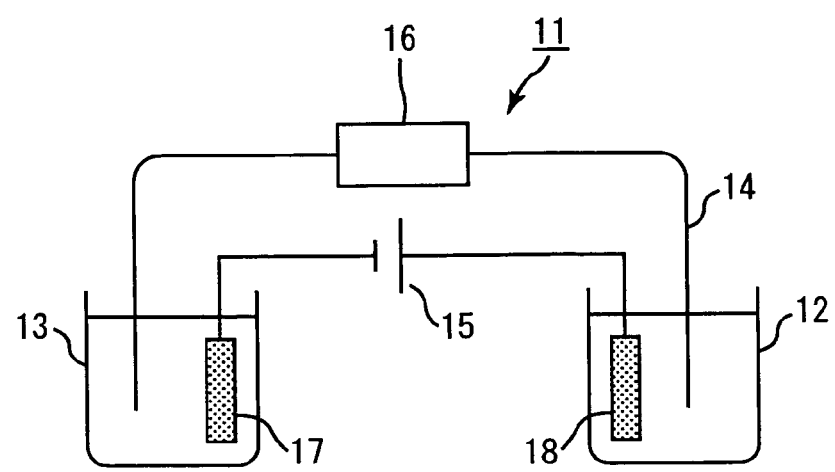
FIG. 7 is a schematic view showing an example of an electrophoresis apparatus that implements the method for measuring hemoglobin of the present invention.

| EXPLANATION OF SYMBOLS | |
| --- | --- |
| 11 | Capillary electrophoresis apparatus |
| 12 | Anode reservoir |
| 13 | Cathode reservoir |
| 14 | Capillary |
| 15 | High-voltage power supply |
| 16 | Detector |
| 17 | Electrode |
| 18 | Electrode |
| 1 | Stable HbA1c |
| 2 | HbA$_0$ |
| 3 | Modified Hb (unstable HbA1c) |
| 4 | HbF (Fetal Hb) |
| 5 | HbS |
| 6 | HbC |
| 7 | HbA2 |

The invention claimed is:

1. A method for measuring hemoglobin using electrophoresis,
   which comprises:
   immobilizing an ionic polymer on an inner surface of a migration path by covalently binding the ionic polymer to the inner surface of the migration path, or heating or drying after contacting the ionic polymer to the inner surface of the migration path; and
   using a buffer solution containing a sulfated polysaccharide.

2. The method for measuring hemoglobin according to claim 1,
   wherein the ionic polymer is an anionic polymer.

3. The method for measuring hemoglobin according to claim 1,
   wherein the ionic polymer is a cationic polymer.

4. A method for measuring stable hemoglobin A1c,
   which comprises using the method for measuring hemoglobin according to claim 1.

5. A method for simultaneously measuring stable hemoglobin A1c and abnormal hemoglobins,
   which comprises using the method for measuring hemoglobin according to claim 1.

6. A method for measuring stable hemoglobin A1c,
   which comprises using the method for measuring hemoglobin according to claim 2.

7. A method for measuring stable hemoglobin A1c,
   which comprises using the method for measuring hemoglobin according to claim 3.

8. A method for simultaneously measuring stable hemoglobin A1c and abnormal hemoglobins,
   which comprises using the method for measuring hemoglobin according to claim 2.

9. A method for simultaneously measuring stable hemoglobin A1c and abnormal hemoglobins,
   which comprises using the method for measuring hemoglobin according to claim 3.

* * * * *